United States Patent [19]

Stengel

[11] 4,158,915
[45] Jun. 26, 1979

[54] ARTIFICIAL DENTURES, AND METHOD AND APPARATUS FOR PREPARING SAME

[76] Inventor: Heinz W. Stengel, 156 Shore Dr., Box 643, Ogden Dunes, Ind. 46368

[21] Appl. No.: 813,503

[22] Filed: Jul. 7, 1977

[51] Int. Cl.² ............................................. A61C 13/00
[52] U.S. Cl. .......................................................... 32/2
[58] Field of Search ......................................... 32/2, 32

[56] References Cited

U.S. PATENT DOCUMENTS

| 3,092,909 | 11/1963 | Miller | 32/32 |
| 3,335,495 | 8/1967 | Wichner | 32/2 |

Primary Examiner—Robert Peshock
Attorney, Agent, or Firm—Olson, Trexler, Wolters, Bushnell & Fosse, Ltd.

[57] ABSTRACT

Artificial dentures, and a method and apparatus for preparing them are disclosed. After a dentition base plate is prepared, a temporary integral strip of gum tissue and supported teeth elements is temporarily fixed to the base plate. The assembly is then locked in a jig, the temporary tooth/gum strip is removed, and a permanent tooth/tissue strip is installed on the base plate in a position providing proper appearance and proper bite relationship with mating dentition. A jig for retaining the base plate in a given location is also provided.

13 Claims, 6 Drawing Figures

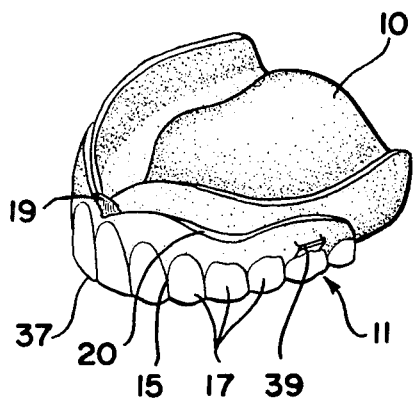
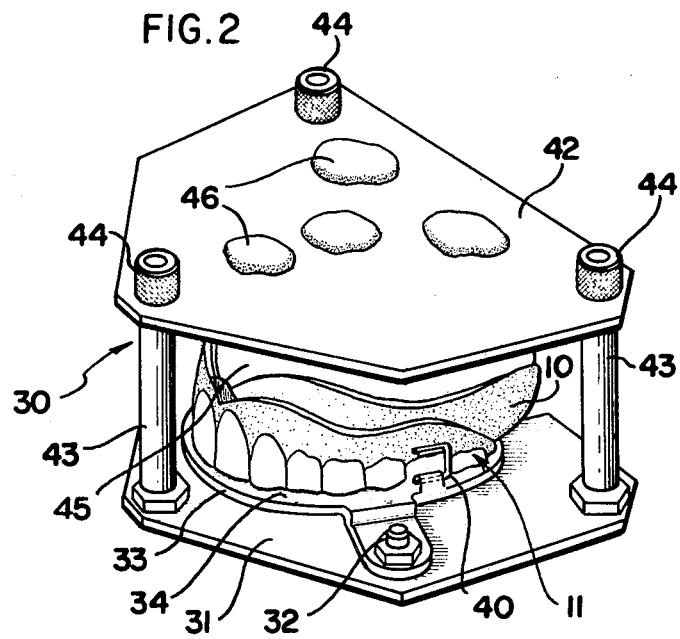
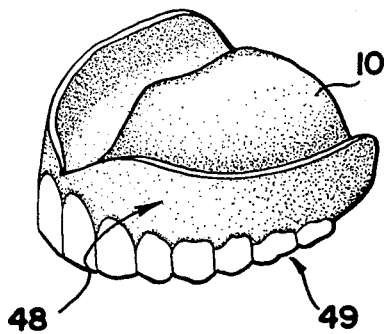
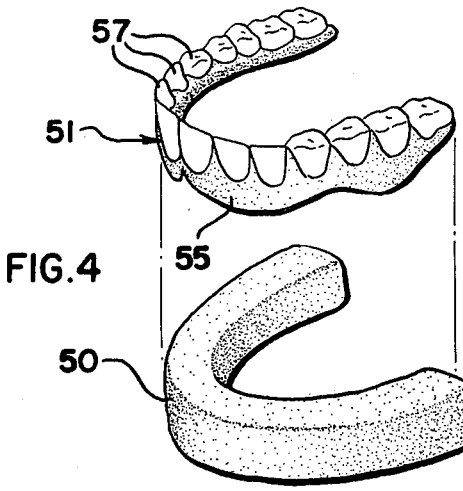
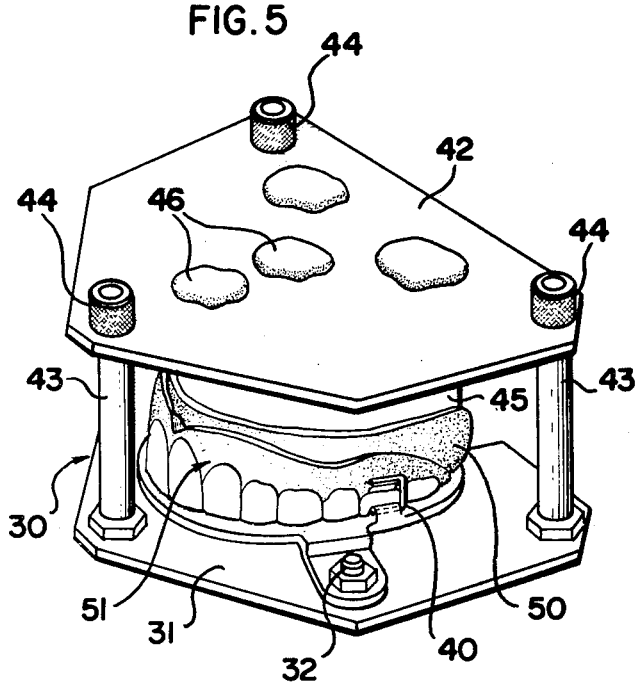
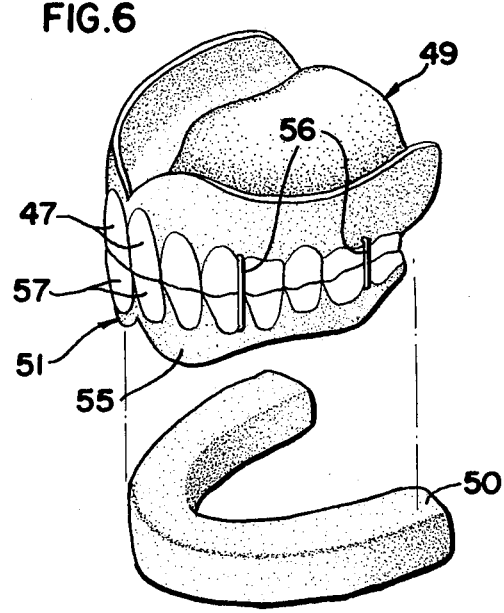

ARTIFICIAL DENTURES, AND METHOD AND APPARATUS FOR PREPARING SAME

BACKGROUND OF THE INVENTION

This invention relates generally to methods and apparatus for preparing artificial dentures, and more particularly concerns a method of preparing false teeth and associated structure which will feel comfortable to the user, appear inconspicuous and natural to the observer, and yet which can be offered to the patient at low cost.

Traditionally, methods of preparing complete or half sets of dentures have been complex, time consuming, and consequently expensive for the patient. These methods, in general, include the following steps:

1. Primary impressions of the patient's mouth are taken with an appropriate impression material.
2. After these impressions are poured in dental stone or plaster, the casts are used to construct custom trays.
3. Final impressions are taken using these custom trays filled with a paste or rubber impression material to obtain a more accurate stone cast of those portions of the patient's mouth which are proximate to or will coact in some way with the artificial dentition to be provided.
4. These final stone casts are fitted with heat molded base plates and wax biterims.
5. The biterims are tried in the patient's mouth and carefully adjusted to proper occlusal plane, length, and lip support. The midline is marked and upper and lower biterims are fixed in the proper centric relations by means of a paste or softened wax.
6. Teeth elements are selected for proper size, shape and shade.
7. The base plate-and-biterim assemblies are fixed in an articulator by means of dental stone or plaster.
8. The artificial teeth elements are individually set into the wax biterims. Each individual tooth is set in softened wax in proper relationship to adjacent teeth, the patient's lips, and into the proper occlusion.
9. Space surrounding the teeth is filled with wax, and the wax is carefully carved to simulate gum tissue.
10. The tooth, biterim and base plate assemblies are now tried into the patient's mouth and are evaluated for proper aesthetics and bite relations. In most cases, this tryin proves unsatisfactory.
11. Corrections are made to each assembly, and further tryins are made until proper fit, bite relation and aesthetics are obtained.
12. A molding post dam is placed into the upper model to compensate for shrinkage of the base material. Both wax set ups are luted with wax to the stone cast. Final carving of the tissue areas is completed.
13. The model portion of the wax denture is invested with plaster in a split metal flask. After the plaster is set and painted with separating medium, the top portion of the flask is filled with dental stone or plaster, and that material is allowed to harden.
14. The flasks are placed in hot water to soften the wax, and the wax is flushed out.
15. A separating medium is painted upon all plaster or stone surfaces, and is allowed to dry.
16. Acrylic, vinyl or other material suitable for denture base use is mixed and packed into the mold.
17. The mold flasks are closed, and clamped in the closed position.
18. The mold flasks are now immersed in water. Both the water and the immersed flasks are then heated gradually to set the denture material.
19. The hot flasks are permitted to cool slowly, the flasks are opened, and the dentures are removed and cleansed of plaster.
20. The dentures are remounted on the articulator to again grind the teeth into proper occlusion. This occlusial reorientation is necessary because of small but noticable distortions of the heat-cured denture base materials.
21. The dentures are now separated from their models, and all remaining stone and plaster is removed with rotary instruments and sandpaper.
22. After final polishing and cleaning, the dentures are delivered to the patient.

From this description, it will be apparent that the present method of constructing dentures is an extremely complicated, time-consuming and expensive undertaking. So expensive, indeed, is this method that many elderly persons living on modest incomes are unable to afford dentures. As a result, many such persons are, quite simply, left without teeth.

It is accordingly the general object of the present invention to provide a relatively inexpensive, quick, and less complex method of preparing dentures.

A more specific object of the invention is to provide a method of preparing dentures which makes effective use of pre-formed tooth and gum tissue elements.

Another object is to provide a method and associated apparatus for preparing artificial dentures which results in a denture end product of attractive, natural appearance and close, comfortable fit for the user.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is a perspective view of a maxillary denture base plate and an attached temporary strip or flange of teeth and underlying tissue used as portions of the artificial dentition of the present invention;

FIG. 2 is a perspective view of the base plate and attached temporary strip of teeth and tissue as they appear when secured within a construction-assisting jig;

FIG. 3 is a perspective view of the maxillary base plate and an attached permanent teeth and underlying tissue;

FIG. 4 is an exploded perspective view of a mandibular base plate and an overlying temporary flange strip of teeth and tissue;

FIG. 5 is a perspective view similar to FIG. 2 but showing the mandibular base plate and associated temporary dentition strip as they appear when secured within the jig; and FIG. 6 is an exploded perspective view illustrating an intermediate step in the preparation of a full set of artificial dentition.

DETAILED DESCRIPTION

While the invention will be described in connection with a preferred embodiment and procedure, it will be understood that it is not intended to limit the invention to this embodiment and procedure. On the contrary, it is intended to cover all alternatives, modifications and equivalents as may be included within the spirit and scope of the invention as defined by the appended claims.

Turning more particularly to the drawings, FIG. 1 illustrates a maxillary base plate 10, to which is attached a one-piece temporary flange or strip 11 representing the maxillary dentition and supporting, adjacent gum tissue. The maxillary base plate 10 can comprise a relatively thin sheet of acrylic, vinyl, or other material which has been adapted to closely conform to the contours of the patient's mouth. This close conformance can be obtained, in known manner, by utilizing a mold impression of the patient's gum and surrounding oral tissues.

In accordance with one aspect of the invention, denture manufacturing costs can be lowered and denture preparation time can be considerably shortened by providing temporary dentition in a continuous tooth/tissue strip 11 comprising a single continuous gum tissue supportive element 15 and a plurality of supported tooth elements 17.

When a full set of artificial maxillary dentition is to be prepared, the maxillary base plate 10 is first tried in the patient's mouth and checked for proper fit. After proper fit has been obtained, the temporary maxillary tooth/tissue strip 11 is temporarily attached to the base plate 10, as by small pads of dental wax 19 or similar material. This attachment material secures the tooth/tissue strip 11 to the base plate 10, and yet easily permits small adjustments to be made between the base plate 10 and strip 11.

After the temporary tooth/tissue strip 11 has been properly located on the base plate 10 so as to afford proper appearance, proper vertical relationship with the supporting base plate, and proper bite relationship with other portions of the patient's dentition, the tooth/tissue strip 11 can be more firmly yet still temporarily affixed to the base plate 10, if desired. In the present instance, this is accomplished by withdrawing the base plate and strip from the patient's mouth, and then introducing an appropriate dental plaster or other temporary adhesive material at convenient points 20 between the wax pads 19 in the spaces between the strip 11 and plate 10.

After the maxillary dentition has been temporarily prepared as described above, this temporary dentition is em placed within a jig 30. To precisely designate relative locations of the temporary dentition defined by the tooth/tissue strip 11, a jig floor 31 is provided with fasteners, such as ordinary threaded screw fasteners 32, to which are attached an occlusal index member 33. This occlusal index member 33 is provided with an upper surface 34 having impressions adapted to mate with the occlusal and incisal surfaces 37 of the temporary dentition teeth elements 17. This index 33 can be selected from a series of indexes providing various dental arch shapes.

To firmly secure the temporary strip 11 and plate 10 within the jig 30, the temporary tooth/tissue strip 11 is provided with at least two small ears 39, and the occlusal index 33 is provided with rotatable catches 40 adapted to engage these ears 39 and so lock the dentition in and upon the occlusal index 33. When the temporary strip and plate are locked into the jig, subsequent dentition preparation steps can be accomplished with diminished fear of accidently or inadvertently causing dentition misalignment. Above the locked-in strip and plate, a jig top 42 is secured upon spacer posts 43 by convenient devices such as knurled nuts 44 in a location spaced above the base plate 10.

Next, into the space between the base plate 10 and the jig top 42 is emplaced a quantity of dental plaster 45. Since the dental plaster 45 is emplaced in a semi-liquid form, appropriate dam members (not shown) of either a permanent or temporary nature can be depended downwardly or extended upwardly from other portions of the jig so as to retain the dental plaster 45 in its place.

The jig top 42 is provided with a number of holes, through which sprues 46 of the dental plaster 45 project. When the plaster 45 sets or hardens, the plaster is secured to the jig top 42 by the hardened sprues 46, and the base place 10 is fixed in place within the jig 30 by the plaster 45.

After the dental plaster 45 has hardened so as to precisely and rigidly affix the dental base plate 10 relative to the jig index 33, the catches 40 are opened, and the temporary tooth/tissue strip 11 is removed. Permanent dentition, which here takes the form of a permanent tooth/tissue strip 48 selected to provide proper gum tissue and tooth enamel coloring. This permanent artificial dentition is then substituted for the temporary strip in the jig. It will be noted that the occlusal and incisal surfaces of the permanent strip 48 can be emplaced precisely at the locations previously occupied by the occlusal and incisal surfaces of the temporary tooth/tissue strip by simply emplacing the occlusal and incisal surfaces of the permanent strip 48 within and upon the index 33. The permanent dentition strip 48 is then positioned, with great precision, in the desired location relative to the base plate 10.

Next, an appropriate dental bonding agent can be poured between the base plate 10 and the permanent tooth/tissue strip 48 so as to permanently bond the tooth/tissue strip 48 to the base plate 10. This bonding agent can be self-curing denture base resin containing acrylic, vinyl, or other compounds. After this bonding agent has cured, the now-unitized base plate 10 and supported teeth elements 47 are removed from the jig 30, and can be ground, polished, and otherwise finished to provide the appearance indicated in FIG. 3. The finished artificial maxillary dentition 49 is then returned to the patient for final tryin.

As illustrated more particularly in FIGS. 4 and 5, a similar process can be used to prepare artificial mandibular dentition. Here, an arch-shaped mandibular base plate 50 is prepared as described above, and a temporary tooth/tissue strip 51 having gum elements 55 and supported teeth elements 57 is temporarily affixed to the base plate 50. As previously described, the strip 55 is attached to the plate 50 in a position to provide proper oral aesthetics and proper bite relationship with surrounding dentition. After the tooth/tissue strip 51 is secured to the base plate 50, the unit is removed from the patient's mouth, inverted, and emplaced within the jig 30 as illustrated in FIG. 5. Again, the temporary tooth/tissue strip is removed and a permanent tooth/tissue strip is substituted into the jig 30. The tooth/tissue strip and the base plate are then permanently bonded together, finished, and returned to the patient for final tryin and subsequent use.

It is another feature of the invention that this method and apparatus can be used to provide even complete sets of artificial dentition at much reduced cost. This is accomplished by first providing the finished maxillary dentition 49 in its permanent form as illustrated in FIG. 6. Thereafter, the permanent maxillary dentition 49 is reinstalled in the patient's mouth, and the mandibular base plate 50 is also installed. In carrying out the invention, the temporary mandibular tooth/tissue strip 51 is thereafter affixed to adjacent portions of the artificial dentition. To insure proper bite relationship between the permanent maxillary and mandibular dentition, the temporary mandibular tooth/tissue strip 51 is first affixed to the permanent tooth elements 47. This is accomplished in the present instance by one or more small staple members 56 adapted to extend between the finished maxillary strip 48 and the temporary mandibular tooth elements 57. After this proper bite relationship is obtained, the mandibular tooth/tissue strip 51 is temporarily affixed to the mandibular base plate 50 as described above. The entire dentition assembly is then removed from the patient's mouth, the staples 56 are removed, and the mandibular assembly 50 and 51 is emplaced in the jig 30. The temporary tooth/tissue strip 51 is then removed and a permanent strip is bonded to the base plate, as described above. After completion, the mandibular dentition and maxillary dentition are returned to the patient for final tryin and use.

The invention is claimed as follows:

1. A method of preparing false teeth, comprising the steps of preparing a base plate conforming to the contours of a portion of a patient's mouth, temporarily affixing a temporary tooth/tissue strip comprising a strip of teeth and gum elements to the base plate, adjusting the strip and base plate into a desired strip-base plate assembly interrelationship providing proper bite relationship with other dentition in the patient's mouth by using a temporary strip-base plate bonding agent, affixing the base plate in one portion of a jig and affixing the attached strip of teeth in another portion of a jig having indexing means so as to define the obtained temporary strip-base plate assembly interrelationship, removing the temporary bonding agent and the temporary tooth/tissue strip from the base plate, while retaining the base plate in the jig, locating a permanent set of teeth and gum elements adjacent the base plate in the desired interrelationship previously defined by the jig, and affixing the permanent set of teeth and gum elements to the base plate with a permanent strip-base plate bond.

2. A method according to claim 1 wherein the step of permanently attaching said permanent set of teeth and tissue elements to the base plate includes the step of permanently attaching at least one permanent tooth strip comprising a plurality of teeth elements and a single tooth supporting gum tissue element to the base plate.

3. A method according to claim 1 including the step of selecting a permanent tooth strip comprising a plurality of tooth representations and a single supportive gum element representation from an array of permanent strips of varying sizes, shapes and colorations.

4. A method according to claim 1 wherein the step of permanently attaching the permanent set of teeth and gum elements to the base plate includes the step of permanently attaching the permanent set of teeth and gum elements to the base plate in the desired interrelationship defined by the jig with an acrylic-containing permanent tooth/tissue strip-base plate bonding agent.

5. A method according to claim 1 wherein the step of permanently attaching the permanent set of teeth and gum elements to the base plate includes the step of permanently attaching the permanent set of teeth and gum elements to the base plate in the desired interrelationship defined by the jig with a vinyl-containing permanent tooth/tissue strip-base plate bonding agent.

6. A method of preparing false teeth, comprising the steps of preparing a maxillary base plate conforming to a contour of a maxillary portion of a patient's mouth, temporarily affixing a temporary maxillary tooth/tissue strip comprising a strip of teeth and gum elements to the maxillary base plate, adjusting the maxillary strip and base plate into a desired strip/base plate interrelationship by using a temporary strip-base plate bonding agent, affixing the maxillary base plate in one portion of a jig and the attached maxillary tooth/tissue strip of teeth in another portion of a jig having indexing means so as to define the obtained temporary strip-base plate interrelationship, removing the temporary bonding agent and the temporary tooth/tissue strip from the maxillary base plate, locating a permanent set of teeth and gum elements in the jig in the position previously occupied by the temporary maxillary tooth/tissue strip, permanently attaching the permanent set of artificial teeth and gum elements to the maxillary base plate in the desired interrelationship defined by the jig with a permanent element-base plate bond, preparing a mandibular base plate conforming to the contours of a mandibular portion of a patient's mouth, re-installing the permanent maxillary base plate and artificial teeth in the patient's mouth, temporarily affixing a temporary mandibular tooth/tissue strip comprising a strip of mandibular teeth and gum tissue elements to the permanent maxillary teeth and gum elements, adjusting the mandibular strip and base plate into a desired bite relationship, affixing the mandibular tooth/tissue strip to the mandibular base plate by using a temporary strip-base plate bonding agent, removing, as a unit, the permanent maxillary artificial dentition and the temporary mandibular artificial dentition from the patient's mouth, removing the permanent maxillary dentition from the temporary mandibular dentition, affixing the mandibular base plate in one portion of a jig and the attached temporary tooth/tissue strip in another portion of the jig so as to define the obtained temporary mandibular strip-mandibular base plate interrelationship, removing the temporary bonding agent and the temporary tooth/tissue strip from the mandibular base plate, locating a permanent set of mandibular teeth and gum elements in the jig in the position previously occupied by the temporary mandibular strip and permanently attaching the permanent set of mandibular teeth and gum tissue elements to the mandibular base plate in the desired interrelationship defined by the jig with a permanent strip-base plate bond.

7. A method according to claim 6 including the step of affixing the mandibular tooth/tissue strip to the permanent maxillary artificial dentition by means of staple elements.

8. A jig for preparing a set of false teeth, comprising in combination, a mold top member, a mold bottom member, and spacer means capable of being affixed to both the mold top and mold bottom members, so as to affix the mold top member and mold bottom member in predetermined immobile positions relative to one another, but spaced apart from one another sufficiently to receive an artificial dentition base plate and artificial temporary teeth affixed to the base plate, permanent index means having impressions adapted to mate with occlusal and incisal surfaces of the temporary artificial teeth in a desired orientation, catch means for securing the temporary teeth on nnd in the index means impressions, and index affixing means for securing the index in a position in the jig which indicates the desired teeth orientation, so as to indicate the desired occlusal and incisal surface orientation when the temporary teeth are removed and replaced with permanent artificial teeth to be permanently affixed to the base plate.

9. A jig according to claim 8 including fastener means for fastening the index means to one of the mold top and mold bottom members.

10. A jig according to claim 8 wherein said index means is affixed to one of said top and bottom members, and wherein said other of said top and bottom members is provided with means for aggressively retaining set dental plaster, and any base plate carried upon said set dental plaster, against said member.

11. A jig according to claim 10 wherein said means for aggressively retaining dental plaster includes orifice means permitting dental plaster sprues to extend through said member.

12. A jig according to claim 8 wherein said spacer means comprise a plurality of post members extending between said jig top member and said jig bottom member.

13. A jig according to claim 12 including removable fastener members associated with said post means to permit one of said jig top and bottom members to be quickly detached from remaining portions of the jig, and precisely re-installed in and upon said remaining portions of the jig and precisely in its original position.

* * * * *